United States Patent
Furutani et al.

[11] Patent Number: 6,071,609
[45] Date of Patent: Jun. 6, 2000

[54] ORGANIC TRIBLOCK COMPOUND SOLID LUBRICANT COMPRISING THE SAME AND MAGNETIC RECORDING MEDIUM

[75] Inventors: Takahiro Furutani, Kyoto-fu; Hideo Daimon, Ibaraki; Sayaka Shinomoto, Kyoto; Kazushi Miyata, Osaka-fu; Tetsuo Mizumura, Ibaraki-ken, all of Japan

[73] Assignee: Hitachi Maxell, Ltd., Osaka-fu, Japan

[21] Appl. No.: 09/015,767

[22] Filed: Jan. 29, 1998

Related U.S. Application Data

[62] Division of application No. 08/572,742, Dec. 14, 1995, Pat. No. 5,750,747.

[30] Foreign Application Priority Data

Dec. 14, 1994 [JP] Japan ..................... 6-333269
Dec. 27, 1994 [JP] Japan ..................... 6-337926

[51] Int. Cl.$^7$ .................................... G11B 5/66
[52] U.S. Cl. ............... 428/332; 428/336; 428/694 T; 428/694 TS; 428/694 TB; 428/694 TP; 428/694 TC; 428/694 TF; 428/694 ST; 428/900
[58] Field of Search ............. 428/694 T, 694 TS, 428/694 TB, 694 TP, 694 TC, 694 TF, 694 ST, 900, 332, 336

[56] References Cited

U.S. PATENT DOCUMENTS

| | | | |
|---|---|---|---|
| 4,828,924 | 5/1989 | Shoji et al. | 428/422 |
| 5,214,216 | 5/1993 | Tohzuke et al. | 568/615 |
| 5,223,342 | 6/1993 | Shoji et al. | 428/413 |
| 5,227,516 | 7/1993 | Tohzuka et al. | 560/182 |
| 5,374,480 | 12/1994 | Nishikawa et al. | 428/336 |
| 5,750,747 | 5/1998 | Furutani | 554/36 |

FOREIGN PATENT DOCUMENTS 6-004855  1/1994  Japan.

*Primary Examiner*—Leszek Kiliman
*Attorney, Agent, or Firm*—Birch, Stewart, Kolasch & Birch, LLP

[57] ABSTRACT

An organic compound of the formula: $R_1$-$Z_1$-$R_3$-$Z_2$-$R_2$ in which $R_1$ and $R_2$ represent a linear, branched or cyclic saturated or unsaturated hydrocarbon group, a polyether group, a polyester group, a polyamide group or a polycarbonate group; $Z_1$ and $Z_2$ represent an amide bond, an ether bond, a urethane bond, a urea bond or an amine salt bond formed by a reaction between an acid and an amine; and $R_3$ is a group of the formula: $-(CH_2)_x-(CF_2)_y-(CH_2)_z-$ in which x and z are an integer of 1 to 4, and y is an integer of 4 to 34 which is useful as a lubricant to be used, for example in a magnetic recording medium.

9 Claims, 1 Drawing Sheet

ORGANIC TRIBLOCK COMPOUND SOLID LUBRICANT COMPRISING THE SAME AND MAGNETIC RECORDING MEDIUM

This application is a divisional of application Ser. No. 08/572,742, filed on Dec. 14, 1995 now U.S. Pat. No. 5,750,747 the entire contents of which are hereby incorporated by reference.

BACKGROUND OF THE INVENTION

1. Field of the Invention

The present invention relates to a novel organic triblock compound, a solid lubricant comprising the same, and a magnetic recording medium comprising a lubricant layer containing said solid lubricant.

2. Description of the Related Art

In general, a ferromagnetic metal thin film type magnetic recording medium, which is produced by coating a ferromagnetic metal or alloy on a non-magnetic substrate by vacuum deposition and so on, is becoming a common magnetic recording medium, since an anti-magnetization of a magnetic layer is easily increased and a thickness of the magnetic layer is easily reduced so that a recording density can be increased in comparison with a coating type magnetic recording medium. However, since the magnetic layer does not contain any binder resin having good toughness, and surface smoothness of the ferromagnetic metal thin layer or a protective layer is very high, a coefficient of friction between the surface of the medium and a magnetic head is increased, so that the magnetic layer is easily abraded or damaged, and therefore its durability and running property are low.

In order to prolong a duration of service of an equipment or apparatus in which a pair of solid parts such as the surface of the ferromagnetic metal thin film type magnetic recording medium and the magnetic head are contacted with low friction and low abrasion, hardening of the solid surface and lubricants have been studied and developed.

In particular, in the field of office automation (OA) equipment, down-sizing is highly required, and a precision mechanism is employed in the sliding portion. As the reduction in size continues, future machines equipment, in which precision parts are continuously or discontinuously moved in a sliding manner under a wide variety of circumstances, friction and abrasion should be further decreased during the start or end of the sliding movement or during the sliding movement, and reduce the load on the motor. To this end, various lubricants are proposed, and tried.

In a conventional protective lubricating system, a surface layer which is hard and less abraded is provided on a sliding part, and a greasy or oily semi-solid or liquid lubricant is used as a lubricant. However, with the improved precision machines or equipment having a much improved smoother contact area, no lubricant exists which that can enable the two contacted solid parts to in a sliding manner move with low friction and low abrasion under any circumstance, for example, at a high or low speed, or under small or large load. Accordingly, the conventional lubricating system cannot compensate for the friction force which results from accidents occurring during an abrupt increase in the start movement or sliding movement.

Consequently, a lubricant to be used in the thin metal film type magnetic recording medium having very high surface smoothness is required to have very strict characteristics which are different from those required for the lubricant used in the coating type magnetic recording medium, and a novel lubricant has been sought.

SUMMARY OF THE INVENTION

An object of the present invention is to provide a novel organic compound which can be used as a lubricant in the metal thin film type magnetic recording medium having a very high surface smoothness.

Another object of the present invention is to provide a metal thin film type magnetic recording medium utilizing such novel organic compound as a lubricant.

According to a first aspect of the present invention, there is provided an organic compound of the formula (1):

$$R_1-Z_1-R_3-Z_2-R_2 \qquad (1)$$

wherein $R_1$ and $R_2$ are the same and different and represent a linear, branched or cyclic saturated or unsaturated hydrocarbon group, a polyether group, a polyester group, a polyamide group or a polycarbonate group each of which has 4 to 34 carbon atoms; $Z_1$ and $Z_2$ are the same or different and represent an amide bond, an ether bond, a urethane bond, a urea bond or an amine salt bond formed by a reaction between an acid and an amine; and $R_3$ is a group of the formula:

$$-(CH_2)_x-(CF_2)_y-(CH_2)_z-$$

in which x and z are the same or different and an integer of 1 to 4, and y is an integer of 4 to 34.

According to a second aspect of the present invention, there is provided a lubricant consisting of the organic compound of the formula (1).

According to a third aspect of the present invention, there is provided a magnetic recording medium comprising a lubricant layer which comprises the organic compound of the formula (1) on a protective layer or in a magnetic layer.

DETAILED DESCRIPTION OF THE INVENTION

Figure 1:
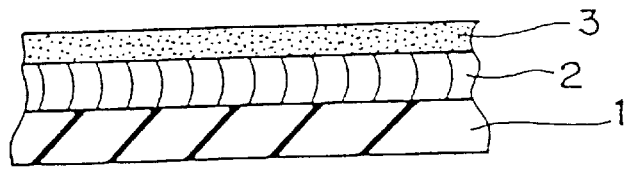
FIGS. 1 to 5 show cross sections of first to fifth examples of the magnetic recording medium according to the present invention, respectively.

In the formula (1), $R_1$ and $R_2$ are the same and different and represent a linear, branched or cyclic saturated or unsaturated hydrocarbon group, a polyether group, a polyester group, a polyamide group or a polycarbonate group each of which has 4 to 34 carbon atoms, preferably 8 to 18 carbon atoms.

When the number of the carbon atoms in $R_1$ or $R_2$ is less than 4, an intermolecular action is weak since the molecular chain length is short, so that a sufficient lubrication property may not be obtained. Preferably, the number of the carbon atoms is at least 6, since a solvent and a concentration of the compound in the solvent can be selected from wide ranges. When the number of the carbon atoms exceeds 34, a lubricating effect is saturated, so that a compound having such large number of carbon atoms is uneconomical. From a practical point of view, the number of the carbon atoms is preferably 18 or smaller.

$Z_1$ and $Z_2$ are the same or different, and selected from the group consisting of an amide bond, an ether bond, a urethane bond, a urea bond or an amine salt bond formed by a reaction between an acid (for example, a carboxylic acid, a sulfonic acid, a phosphoric acid, etc.) and an amine. In addition, other bond which can bond each end of the center block and the $R^1$ and $R^2$ group may be used.

$R_3$ is a group of the formula:

$$-(CH_2)_x-(CF_2)_y-(CH_2)_z-$$

in which x and z are the same or different and an integer of 1 to 4, and y is an integer of 4 to 34, preferably 6 to 18.

When y is less than 4, an intermolecular action is weak since the chain length of $(CF_2)_y$ is short, so that a specific lubrication property of the fluorine atoms may not be obtained. Preferably, y is at least 6, since the specific lubrication property of the fluorine atoms is obtained. When y exceeds 34, a lubricating effect is saturated, so that a compound having such long $(CF_2)_y$ group is uneconomical. From a practical point of view, y is preferably 18 or smaller.

Each of x and z is an integer of 1 to 4. If the $R_3$ block does not include any —$CH_2$— group, the compound may have the same lubrication property. But, when no —$CH_2$— group is present, the $Z_1$ and $Z_2$ bonds which bond the $R_3$ group and the $R_1$ and $R_2$ groups tend to be easily cleaved under severe conditions because of the strong electronegativity of the $(CF_2)_y$ group. When the —$CH_2$— group is inserted between the $(CF_2)_y$ group and the $Z_1$ and $Z_2$ bonds, it can relax the strong electronegativity so that decomposition of the compound is suppressed. This effect can be attained by at least one —$CH_2$— group. When the number of —$CH_2$— groups exceeds 4, the effect is saturated.

The compound of the formula (I) may be prepared by any of conventional methods. One of the industrial synthesis methods is as follows:

A fluorine compound having, at its molecular ends, functional groups such as hydroxy groups, carboxyl groups, acid halide groups, ester groups, amino groups, isocyanate groups or epoxy groups is reacted with a non-fluorine compound having, at its molecular end, a functional group which can react with the functional groups of the fluorine compound such as a halogen atom, a hydroxy group, a carboxyl group, an amino group, an isocyanate group or an epoxy group are reacted via a reaction between functional groups to chemically bond two compounds through an amide bond, an ether bond, a urethane bond, a urea bond or an amine salt bond.

Typical preparation methods of the compound (I) having such bond will be explained.

I. When $Z_1$ and $Z_2$ are amide bonds:

(I-1) A fluorine-containing diamine having amino groups at both molecular ends represented by the formula (2):

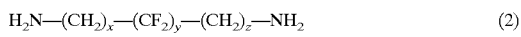

$$H_2N—(CH_2)_x—(CF_2)_y—(CH_2)_z—NH_2 \quad (2)$$

wherein x, y and z are the same as defined above is reacted with an acid chloride of the formula (3):

$$RCOCl \quad (3)$$

wherein R is a linear, branched or cyclic saturated or unsaturated hydrocarbon group, a polyether group, a polyester group, a polyamide group or a polycarbonate group each of which has 4 to 34 carbon atoms according to the following reaction formula (4):

$$H_2N—(CH_2)_x—(CF_2)_y—(CH_2)_z—NH_2+2RCOCl→RCONH—(CH_2)_x—(CF_2)_y—(CH_2)_z—NHCOR \quad (4).$$

The acid chloride can be prepared from a carboxylic acid and thionyl chloride and so on by a conventional method (I-2) An acid chloride of a fluorine-containing dicarboxylic acid having carboxyl groups at both molecular ends represented by the formula (5):

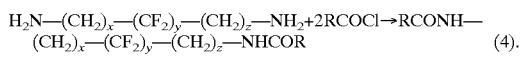

$$ClCO—(CH_2)_x—(CF_2)_y—(CH_2)_z—COCl \quad (5)$$

wherein x, y and z are the same as defined above is reacted with an amine of the formula (6):

$$RNH_2 \quad (6)$$

wherein R is the same as defined above according to the following reaction formula (7):

$$ClCO—(CH_2)_x—(CF_2)_y—(CH_2)_z—COCl+2RNH_2→RNHOC—(CH_2)_x—(CF_2)_y—(CH_2)_z—CONHR \quad (7)$$

II. When $Z_1$ and $Z_2$ are ether bonds:

A fluorine-containing dialcohol having hydroxyl groups at both molecular ends represented by the formula (8):

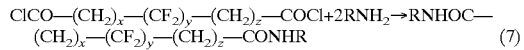

$$HO—(CH_2)_x—(CF_2)_y—(CH_2)_z—OH \quad (8)$$

wherein x, y and z are the same as defined above is reacted with a halide of the formula (9):

$$RX \quad (9)$$

wherein R is the same as above, and X is a halogen atom such as a chlorine atom, a bromine atom or an iodine according to the following reaction formula (10):

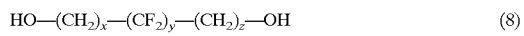

$$HO—(CH_2)_x—(CF_2)_y—(CH_2)_z—OH+2RX→RO—(CH_2)_x—(CF_2)_y—(CH_2)_z—OR \quad (10)$$

III. When $Z_1$ and $Z_2$ are urethane groups:

The fluorine-containing dialcohol of the formula (8) is reacted with an isocyanate of the formula (11):

$$RNCO \quad (11)$$

wherein R is the same as defined above according to the following reaction formula (12):

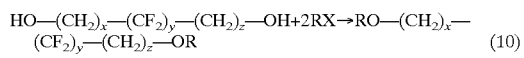

$$HO—(CH_2)_x—(CF_2)_y—(CH_2)_z—OH +2RNCO→RNHCOO—(CH_2)_x—(CF_2)_y—(CH_2)_z—OCONHR \quad (12)$$

IV. When $Z_1$ and $Z_2$ are urea bonds:

The fluorine-containing diamine of the formula (2) and the isocyanate of the formula (11) are reacted according to the following reaction formula (13):

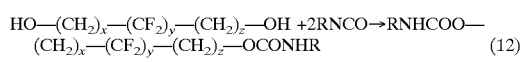

$$H_2N—(CH_2)_x—(CF_2)_y—(CH_2)_z—NH_2+2RNCO→RNHCONH—(CH_2)_x—(CF_2)_y—(CH_2)_z—NHCONHR \quad (13)$$

V. When $Z_1$ and $Z_2$ are amine salt bonds:

A fluorine-containing dicarboxylic acid having carboxyl group at both molecular ends represented by the formula (14):

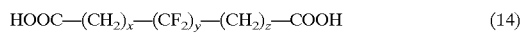

$$HOOC—(CH_2)_x—(CF_2)_y—(CH_2)_z—COOH \quad (14)$$

wherein x, y and z are the same as defined above is reacted with the amine of the formula (6) according to the following reaction formula (15):

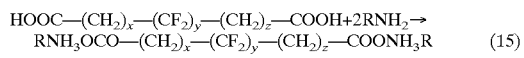

$$HOOC—(CH_2)_x—(CF_2)_y—(CH_2)_z—COOH+2RNH_2→\\RNH_3OCO—(CH_2)_x—(CF_2)_y—(CH_2)_z—COONH_3R \quad (15)$$

The compound of the formula (1) is preferably used as a lubricant. This lubricant can prevent seizing or sticking between two solid materials which are moving in a sliding manner solve the problem that the friction force abruptly increases accidentally in the case of starting failure or during sliding movement, and provides a stable sliding movement property.

Since the lubricant of the present invention comprises the non-fluorine blocks which are bonded to the fluorine block, it can be dissolved in a non-fluorine solvent though it is a fluorine-containing lubricant.

Examples of the solvent in which the lubricant of the present invention is soluble are aliphatic hydrocarbons (e.g. n-hexane, n-heptane, n-octane, n-decane, n-dodecane), aromatic hydrocarbons (e.g. benzene, toluene, xylene, etc.), cyclic hydrocarbons (e.g. cyclohexane, etc.), ketones (e.g. acetone, methyl ethyl ketone, methyl isobutyl ketone, etc.), alcohols (e.g. methanol, ethanol, isopropanol, etc.), ethers (e.g. diethyl ether, cyclohexanone, tetrahydrofuran), and so on.

These solvents are much cheaper than the fluorine solvents. Since these solvents are fluorine free, they do not pollute an air and cause no environmental problem such as destruction of the ozone layer.

The lubricant of the present invention may have, at one or both of the molecular ends, a functional group such as —OH, —COOH, —NH$_2$, —Cl, —Br, —I, —SH, —CH$_2$OCH$_3$, —ONa, —COONa, —SO$_3$Na, and the like. Since these functional groups have a high polarity and function to adhere the compound molecules to the sliding part such as the magnetic layer or the protective layer of the magnetic recording medium, the life of the magnetic recording medium is prolonged.

In the case of the magnetic recording medium, generally a protective layer is formed on a magnetic layer to protect the magnetic layer or to improve the sliding movement. The protective layer may comprise at least one material selected from the group consisting of carbon, SiC$_p$, BN$_p$, CB$_q$, SiN$_q$, CN$_q$, SiO$_r$, ZrO$_r$, TiO$_r$, AlO$_s$, SiM$_w$O$_v$, Fe$_3$O$_4$, Cr$_2$O$_3$, Co$_3$O$_4$, Fe$_2$O$_3$, CoCr$_2$O$_4$, and NiCr$_2$O$_4$ wherein 0.8<p<1.2, 1.0<q<4.8, 1.6<r<2.0, 1.2<s<1.5, 1.6<v<2.0, 0.05<w<0.5, and M is an at least one element selected from carbon, nitrogen or boron. Such protective layer may be used on either of the coating type and metal thin film type magnetic recording media.

The above protective layer has a Vickers hardness of 1000 or more and is chemically stable. In addition, since it is dense, and a self-diffusion coefficient of each element constituting the protective layer is less than 1×10$^{-9}$ cm$^2$/sec., its electric conductivity is low so that it has high corrosion resistance.

The protective layer is preferably formed by a chemical deposition method such as a plasma CVD (chemical vapor deposition) method.

A physical deposition method such as vacuum deposition or sputtering is less preferred, since the protective layer formed by the physical deposition has a large particle size, and the flow of the deposited particles is uneven, so that the adhesion of the deposited particles on a surface having minute flaws is not good, and a protective layer having high coverage cannot be formed.

In chemical deposition methods, such as the plasma CVD method, a monomer gas is decomposed in a plasma to form radicals or ions of molecules or atoms, and the radicals or ions are bond to the surface of a substrate to form a protective layer. Therefore, the deposited particles have small sizes and their flow has low directivity, so that the adhesion of the deposited particles on the surface having minute unevenness is good, and the protective layer with a high covering rate is formed.

The thickness of the hard protective layer is preferably from 50 to 500 Å. When the thickness is less than 50 Å, it is difficult to form a protective layer having no defects, thereby creating insufficient protection as a gas barrier function against moisture and oxygen. When the thickness exceeds 500 Å, the effects are saturated. When the protective layer is formed on the thin metal film type magnetic recording medium, an upper limit of the thickness is preferably 300 Å. When the thickness exceeds 300 Å, a spacing loss between the magnetic head and the medium increases, and the recording-reproducing characteristics are deteriorated.

In particular, a protective layer comprising SiM$_w$O$_v$, wherein M, w and v are the same as defined above, is preferred. While this material is used as the protective layer of the magnetic layer, it can be used as a back face protective layer on a reverse surface of the non-magnetic substrate.

Japanese Patent KOKAI Publication No. 12568/1994 discloses the use of a film of silicon oxide (SiO$_x$ in which 1.5<x<2.0) as an inorganic protective layer of a hard disc. In the case of the magnetic tape on which an external force by stretching, bending, etc. is applied constantly, microcracks are formed in the SiO$_x$ film. For example, when a corrosion test is carried out at 60° C., 90% RH, water and oxygen penetrate in the microcracks, so that a hydroxide of cobalt appears on the surface of the protective layer. Therefore, insufficient anti-corrosion effect is shown.

To solve this problem, the present invention uses SiM$_w$O$_v$, as a material of the protective layer, since a film of this oxide has better stretchability and flexibility than conventional SiO$_x$. A protective layer of SiM$_w$O$_v$ can be used with a flexible magnetic recording medium such as a magnetic tape and a floppy disc, in addition to a fixed magnetic disc such as for a hard disc.

To form the Si—M—O protective layer, the plasma CVD method is preferably used, since the flow of the deposited particles is uniform, and a high covering rate is achieved. Examples of a monomer gas to be used in the plasma CVD method are (1) (for Si———O) a mixture of SiH$_4$, O$_2$ and a volatile hydrocarbon; a mixture of R'$_a$H$_{3-a}$Si—O—SiH$_{3-a}$R'$_a$ wherein R' is a C$_1$–C$_6$ hydrocarbon or fluorinated hydrocarbon group and a is 1, 2 or 3, and O$_2$; a mixture of Si(OCH$_3$)$_4$ or Si(OC$_2$H$_5$)$_4$ and O$_2$; (2) (for Si—N—O) a mixture of SiH$_4$, O$_2$ and N$_2$; a mixture of R'$_a$H$_{3-a}$Si—O—SiH$_{3-a}$R'$_a$ wherein R' and a are the same as defined above, O$_2$ and N$_2$; a mixture of Si(OCH$_3$)$_4$ or Si(OC$_2$H$_5$)$_4$, O$_2$ and N$_2$, and (3) (for Si—B—O) a mixture of SiH$_4$, O$_2$ and B$_2$H$_6$; a mixture of R'$_a$H$_{3-a}$Si—O—SiH$_{3-a}$R'$_a$ wherein R' and a are the same as defined above, O$_2$ and B$_2$H$_6$; a mixture of Si(OCH$_3$)$_4$ or Si(OC$_2$H$_5$)$_4$, O$_2$ and B$_2$H$_6$.

As a carrier gas, helium, neon, argon, krypton or a mixture of such inert gas and hydrogen gas (H$_2$) is used. A total pressure of the monomer mixture and the carrier gas is adjusted to 5 to 200 mTorr.

To generate the plasma, an alternating current of 10 kHz to 13.56 MHz may be used. Alternatively, a microwave having a frequency of 2.45 GHz may be superimposed on the alternating current.

An amount of C, N or B is preferably from 5 to 50 atomic %, more preferably from 10 to 20 atomic % based on silicon. When this amount is less than 5 atomic %, flexibility of the protective layer is not attained, while when it exceeds 50 atomic %, the protective layer becomes hard, and loses flexibility.

When "v" in the above formula is less than 1.6, sufficient hardness as a silicon oxide is not attained, while when it exceeds 2.0, a content of oxygen is excessive so that the layer becomes fragile.

The thickness of the Si—M—O protective layer is preferably from 50 to 300 Å. When the thickness is less than 50 Å, the thin film has defects, so that it loses its ability to form a barrier against water or oxygen gas. When the thickness exceeds 300 Å, a spacing loss between the magnetic head and the recording medium increases, so that the recording-reproducing characteristics deteriorate.

When the protective layer is formed by the plasma CVD method, its adhesion to the underlying magnetic layer is improved. For example, cobalt oxide (CoO) present on the surface of the Co base magnetic layer easily chemically absorbs water in the air to form cobalt hydroxide $Co(OH)_2$. Cobalt hydroxide has a laminated structure in which $Co^{2+}$ ion layers and OH— ion layers are laminated by weak hydrogen bonds. Its crystal system is $CdI_2$.

When the hard protective layer is formed on such surface by the physical deposition method, it is easily peeled off by the external force, since the bonding force of the $Ca(OH)_2$ is weak. Since the plasma CVD method has an etching function, the cobalt hydroxide layer having the weak bonding force can be removed in an early stage of the film formation. Accordingly, the adhesion force of the protective layer to the magnetic layer is greatly increased, so that the durability and corrosion resistance of the magnetic layer are improved.

To realize the etching function, it is effective to mix a reducing hydrogen gas in the raw material gas used in the plasma polymerization, or to generate a negative bias on the substrate side using the above high frequency wave, whereby the kinetic energy of the reactive particles is increased during the film formation.

By the etching function, the non-magnetic CoO layer is also removed from the surface of the magnetic layer in addition to the $Co(OH)_2$ layer. This etching function can be confirmed by measuring a composition of a sample after the formation of the protective layer in the depth direction from the surface of the layer by Auger electron spectroscopy (AES). With a sample having no protective layer, the non-magnetic CoO layer, in which an atomic ratio of Co to O is less than 1, is present on the outermost surface of the magnetic layer.

When the sample having the Si—M—O protective layer formed by the CVD method is analyzed by AES in the depth direction, after the decrease of Si and O peaks in the surface layer, an intermediate layer having a Co/O ratio of larger than 1 (one) appears, and thereafter the mother alloy composition of the magnetic layer appears. From this result, it is confirmed that, when the protective layer is formed by the above method according to the present invention, the etching function decreases the thickness of the non-magnetic or weakly magnetic layer which has been present on the magnetic layer before the formation of the protective layer.

When no etching function is present during the formation of the protective layer, an effective thickness of the non-magnetic layer is the sum of the thickness of the protective layer and that of the non-magnetic oxide layer having the Co/O ratio of smaller than 1 (one) which is present on the magnetic layer. In the present invention, since the thickness of the non-magnetic oxide layer which is present on the magnetic layer is decreased by the etching function during the formation of the protective layer, the effective thickness of the non-magnetic layer is decreased in comparison to the effective thickness obtained in the absence of the etching function.

Accordingly, when the protective layer is formed according to the present invention, an effective space between the magnetic head and the recording medium can be decreased, the spacing loss is reduced during recording and reproducing, and in particular the recording-reproducing characteristics in the short wavelength range can be improved. When the etching function is insufficient during the formation of the Si—M—O protective layer, the surface of the magnetic layer is plasma etched in an atmosphere of argon or hydrogen to forcibly remove the non-magnetic CoO layer present on the magnetic layer before the formation of the protective layer.

To further improve the corrosion resistance of the magnetic recording medium, the Si—M—O layer is formed between the non-magnetic substrate and the cobalt magnetic layer as an intermediate or primer layer, or formed on the back face of the non-magnetic substrate as the back face protective layer or the back coating layer.

In the field of the magnetic tapes, as a substrate for the cobalt magnetic layer, an organic film such as a polyethylene terephthalate film, an aramide film or a polyethylene naphthalate film is used. Such polymer film has larger voids than a molecular size of water or oxygen (2.0 to 4.3 Å). When the magnetic layer is directly formed on the organic polymer film substrate, water and oxygen are supplied to the magnetic layer not only from the surface side but also the substrate film side, and the corrosion proceeds from the back face of the magnetic layer.

The formation of the Si—M—O intermediate layer or back coating layer at the interface between the organic polymer film substrate and the magnetic layer increases the gas barrier function, so that the corrosion from the back face of the magnetic layer can be suppressed.

Preferably, the Si—M—O intermediate (primer) layer or back coating layer (back face protective layer) is formed by the plasma CVD method for the same reason as explained above in connection with the formation of the protective layer. While the physical deposition method can achieve the similar effect, the plasma CVD method can produce the film having less defects and decrease a thickness of the film. A thickness of the intermediate layer or back coating layer is preferably from 50 to 1000 Å. When the thickness is less than 50 Å, a sufficiently continuous film is not formed so that the sufficient barrier function against water and oxygen is not achieved, while when it exceeds 1000 Å, the effect is saturated.

As explained above, the lubricant layer comprising the compound of the formula (1) can be formed directly on the magnetic layer of the magnetic recording medium, while it is preferably formed on the protective layer which is formed on the magnetic layer.

A coating solution of the lubricant can be prepared by dissolving the compound of the formula (1) in the non-fluorine solvent, and is coated on the protective layer and dried by evaporating the solvent to form the lubricant layer on the protective layer.

Alternatively, the lubricant comprising the compound of the formula (1) is contained in the back coating of the magnetic recording medium and then transferred to the magnetic layer and the protective layer.

The lubricant may be coated on the back face of the non-magnetic substrate or mixed in the back coating layer. Further, in the case of the coating type magnetic recording medium, the lubricant can be coated on the magnetic layer or compounded in a magnetic paint of the magnetic layer.

To stably apply the lubricant to the magnetic layer or the protective layer, the magnetic layer or the protective layer may be treated by heat, light such as UV-light, or a plasma of argon or oxygen, before or after the formation of the lubricant layer.

After the application of the lubricant, an excessive lubricant may be removed by washing with the solvent.

The lubricant can be coated on the protective layer by any of conventional coating methods such as dip coating, gravure coating, spray coating or vapor deposition coating. By such coating method, the molecules of the lubricant compound can be absorbed on the surface of the hard protective layer.

Since the bond between the lubricant molecules and the surface of the hard protective layer is mainly the hydrogen bond, the bond energy between them is small, for example, from 20 to 30 kJ/mol. To increase the bond force between them and prevent peeling of the lubricant layer due to sliding movement, it is effective to irradiate the lubricant layer by UV-light having a wavelength of 190 nm or shorter after coating the lubricant layer on the protective layer, whereby the lubricant molecules are chemically bonded to the protective layer, and then the friction and abrasion characteristics are further improved. The irradiation of the UV-light is effective for lubricant molecules having a C-F bond.

Preferably, the wavelength of the UV-light to be irradiated is from 100 nm to 190 nm. The shortest wavelength of practically used UV-light is 100 nm. Since the energy of UV-light having the wavelength longer than 190 nm is smaller than the work function of the hard protective layer, no photoelectron is liberated from the hard protective layer. Therefore, the UV-light having a wavelength longer than 190 nm cannot induce a photochemical reaction between the protective layer and the fluorine-containing lubricant molecule through photoelectrons, and as the result, the molecule of the fluorine-containing lubricant cannot be chemically bonded to the surface of the protective layer.

When the UV-light is irradiated, the atmosphere in a treating room should not contain oxygen, since oxygen is converted to ozone by the UV-light having the wavelength of 185 nm, and ozone decomposes the lubricant molecules. Accordingly, the treating room should have an oxygen-free atmosphere such as an atmosphere of an inert gas, for example, argon.

When the sample having the coated lubricant is heat treated at a temperature of 50 to 100° C. prior to the irradiation of the UV-light, the sliding movement property is further improved. This may be because the molecules of the lubricant diffuse over the surface of the protective layer by the heat energy of the heat treatment, so that the covering rate of the lubricant molecules before the UV-light irradiation is increased.

By the UV-light irradiation, the lubricant layer of the compound which has the (non-fluorinated block)-$Z_1$-(fluorinated block)-$Z_2$-(non-fluorinated block) structure is chemically bonded to the hard protective layer.

The ratio of the chemically bonded lubricant molecules to the coated lubricant is in a specific preferred range. Herein, as the amount of the chemically bonded lubricant is the amount present on the protective layer after ultrasonic washing in n-hexane for 10 seconds is used. Before and after the ultrasonic washing in n-hexane for 10 seconds, the sample is analyzed by the XPS (X-ray photoelectron spectroscopy) using 5500-MC manufactured by Perkin-Elmer. Preferably, a ratio of the intensity of fluorine peak after washing to that before washing is from 0.05:1 to 0.65:1. When this ratio is smaller than 0.05:1, the amount of the chemically bonded lubricant molecules is too small, so that the lubrication characteristics cannot be further improved, while when it exceeds 0.65:1, an amount of the free lubricant molecules which is simply physically absorbed is too small so that the lubrication characteristics deteriorates.

In the field of the magnetic tape and magnetic disc, a substrate having an uneven surface is used to prevent sticking of the magnetic tape to a cylinder or adhesion of the tape or disc to the magnetic head. For example, the magnetic tape comprises a base film having an easy-sliding particle layer on its surface. When the magnetic layer is formed on the base film, the surface of the magnetic layer is uneven so that the ability to slide is improved, and yet the magnetic layer has many defects, so the corrosion resistance of the magnetic tape is severely deteriorated.

As described above, the lubricant comprising the compound of the formula (1) can prevent the sticking and greatly reduce the load during the sliding movement of the magnetic medium. Accordingly, when this lubricant is used, the base film may have a smooth surface, and in turn, the corrosion resistance of the magnetic medium can be improved.

As the base film of the magnetic tape, preferably a polyethylene terephthalate (PET) film having a thickness of less than 6.5 μm, more preferably a polyethylene naphthalate (PEN) film having a thickness less than 6.5 μm, and an aramide film are used to increase the capacity of the magnetic tape. Since the PEN film and the aramide film have a higher stiffness (Young's modulus) and can be made thinner than the PET film, they can advantageously provide for a magnetic tape having a larger capacity than a the PET film.

Preferably, the base film has a surface roughness of 0.5 to 1.5 nm in terms of Ra, and 3.0 to 12.0 nm in terms of Rz. Currently, it is difficult to produce a base film having Ra of less than 0.5 nm and Rz of less than 3.0. When Ra and Rz exceed 1.5 nm and 12.0 nm, respectively, the number of defects of the magnetic layer formed on the base film increases so that the sufficient corrosion resistance cannot be achieved.

The lubricant of the present invention can be used with any kind of the magnetic recording medium, for example, the thin metal film type magnetic recording media and the coating type magnetic recording media. The lubricant of the present invention is preferably used with the thin metal film type recording media.

As the non-magnetic substrate, any one of non-magnetic substrates which are used in the conventional magnetic recording media may be used. Examples of materials of the non-magnetic substrate are synthetic resins (e.g. polyethylene terephthalate, polyethylene naphthalate, polycarbonate, polyimide, polyvinyl chloride, etc.), metals (e.g. aluminum, aluminum alloys, titanium, titanium alloys, etc.), ceramics (e.g. alumina glass, etc.), hard substrates (e.g. glass), and so on. When a hard substrate is used, its surface may be hardened by the application of an oxide coating film such as an aluminum oxide coating film or a Ni—P coating film, or mirror finished.

The shape of the substrate is not limited, and any of a tape, a sheet, a disc, a card and a drum may be used, as long as it can be slidingly contacted to the magnetic head.

Also a kind of the magnetic material for forming the magnetic layer is not limited, and any of the conventionally used magnetic materials may be used.

Examples of the magnetic material for the thin metal film type magnetic recording medium are Co, Ni, Fe, Co—Ni, Co—P, Co—Ni—P, Fe—Co—B, Fe—Co—Ni, Fe—Co—Ni—B, Fe—Ni, Fe—Co, Co—Pt, Co—Ni—Pt, Co—Cr, and these materials to which oxygen is added. Among them, the material comprising 50 atomic % or more of cobalt is preferred.

In the case of the metal thin film type magnetic recording medium, the magnetic layer may be formed by any of conventional methods such as vacuum deposition, ion plating, sputtering, plating, and so on. A thickness of the metal thin film is not limited particularly, and it is in general from 0.03 to 1 μm.

Examples of the magnetic material for the coating type magnetic recording medium are metal oxide magnetic powders (e.g. γ—$Fe_2O_3$, $Fe_3O_4$, an intermediate iron oxide of γ—$Fe_2O_3$ and $Fe_3O_4$, cobalt-containing γ—$Fe_2O_3$, cobalt containing $Fe_3O_4$, $CrO_2$, barium ferrite, etc.), metal powders (e.g. Fe, Co, Fe—Ni—Cr alloys, etc.), metal nitride powders (e.g. iron nitride, etc.), and so on.

In the case of needle-shape particle magnetic powder, preferably, its average particle length (longer axis) is from 0.2 to 1 μm, and an axis ratio (average longer axis/average shorter axis) is from 5 to 10. In the case of a plate-shape particle magnetic powder, preferably its average longer axis is from 0.07 to 0.3 μm.

As a binder resin for binding such magnetic powder, any of conventionally used binder resins may be used. Examples of the binder resin are vinyl chloride-vinyl acetate copolymers, cellulose resins, polyurethane resins, polyester resins, polyvinyl butyrate resins, polyacrylate resins, epoxy resins, phenol resins, polyisocyanate resins, and so on.

In the magnetic recording medium according to the present invention, an intermediate layer may be formed between the non-magnetic substrate and the magnetic layer. For example, on the surface of the non-magnetic substrate, a primer layer of a non-magnetic material having a low melting point (e.g. Si, Ti, Bi, Sn, Pb, Sb, Ga, Ge, In, etc.) is beforehand formed, and the ferromagnetic metal is vertically or obliquely deposited with diffusing the non-magnetic material in the magnetic layer, whereby the non-magnetic material is in-plane formed, and anti-magnetization is increased.

When the magnetic recording medium of the present invention has the magnetic layer only on one surface of the non-magnetic substrate, it can have a back coating layer on the reverse surface. For example, the back coating layer is formed by mixing and dispersing a non-magnetic material (e.g. carbon black, calcium carbonate, etc.), a binder resin (e.g. vinyl chloride-vinyl acetate copolymers, polyurethane resins, cellulose resins, etc.), and an organic solvent to prepare a back coating paint, coating this paint on the reverse surface of the non-magnetic substrate, and drying it.

FIG. 1 shows a cross section of a first example of the magnetic recording medium according to the present invention, which comprises a non-magnetic substrate 1, a magnetic layer 2, and a lubricant layer 3 comprising the compound of the formula (1).

Figure 2:
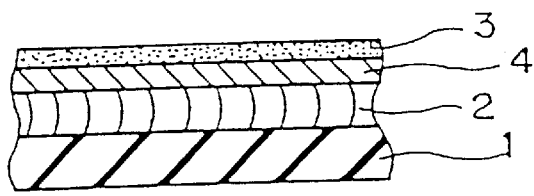

FIG. 2 shows a cross section of a second example of the magnetic recording medium according to the present invention, which further comprises a protective layer 4 of, for example, Si—M—O between the magnetic layer 2 and the lubricant layer 3.

Figure 3:
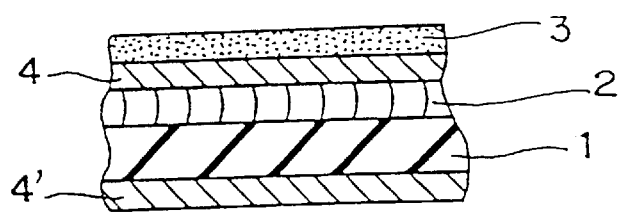

FIG. 3 shows a cross section of a third example of the magnetic recording medium according to the present invention, which further comprises another protective layer 4' of, for example, Si—M—O on the reverse surface of the non-magnetic substrate 1.

Figure 4:
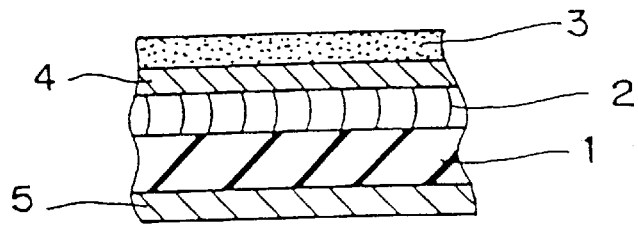

FIG. 4 shows a cross section of a fourth example of the magnetic recording medium according to the present invention, which further comprises a back coating layer 5 on the reverse surface of the non-magnetic substrate 1.

Figure 5:
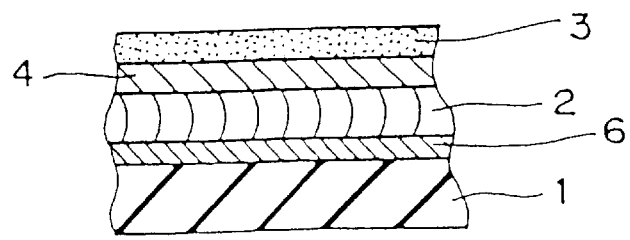

FIG. 5 shows a cross section of a fifth example of the magnetic recording medium according to the present invention, which additionally has a primer layer 6 between the non-magnetic substrate 1 and the magnetic layer 2.

The triblock compound of the formula (1) according to the present invention can be used as a paint resin (a corrosion-proof lining, non-adhesive coating, weathering paint, etc.), a fiber-treatment agent (water and oil repellent), a releasing agent, an oil-resistant agent for paper, a levelling agent, an adhesive, a fire-extinguisher, a cladding of an optical fiber, an optical lens, a medical polymer, and so on.

EXAMPLES

The present invention will be illustrated by the following Examples, which do not limit the scope of the present invention in any way. In Examples, a melting point was measured with RS-1000 (manufactured by Perkin-Elmer) by heating a compound from −20° C. at a heating rate of 5° C./min., and a boiling point was measured with TG 8110 (manufactured by RIGAKU).

Synthesis of triblock compound

Example 1

In toluene (800 g), 1H,1H,10H,10H-perfluoro-1,10-decanediamine (0.5 mole), lauryl chloride (1.2 moles) and pyridine (0.5 moles) were reacted at 100° C. for 6 hours. After cooling, the reaction mixture was diluted by water, and an organic layer was separated, washed with an aqueous solution of sodium hydrogen carbonate, and dried over magnesium sulfate, followed by evaporation off of the solvent. The residue was purified by recrystallization or distillation to obtain a triblock compound 1 of the formula:

M. P. 62–64° C.

Example 2

In the same manner as in Example 1 except that stearyl chloride (1.2 moles) was used in place of lauryl chloride, the reaction was carried out to obtain a triblock compound 2 of the formula:

M. P. 108–110° C.

Example 3

In the same manner as in Example 1 except that linolyl chloride (1.2 moles) was used in place of lauryl chloride, the reaction was carried out to obtain a triblock compound 3 of the formula:

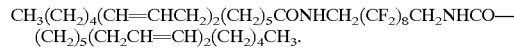

B. P. 220–222° C./1 mmHg.

Example 4

In the same manner as in Example 1 except that 2,3,4-trimethyl-2-neopentyl chloride (1.2 moles) was used in place of lauryl chloride, the reaction was carried out to obtain a triblock compound 4 of the formula:

B. P. 189–190° C./2 mmHg.

Example 5

In the same manner as in Example 1 except that benzoyl chloride (1.2 moles) was used in place of lauryl chloride, the reaction was carried out to obtain a triblock compound 2 of the formula:

M. P. 75–77° C., $C_6H_5CONHCH_2(CF_2)_8CH_2NHCOC_6H_5$.

Example 6

In the same manner as in Example 1 except that cyclohexanecarboxylyl chloride (1.2 moles) was used in place of lauryl chloride, the reaction was carried out to obtain a triblock compound 6 of the formula:

$C_6H_{11}CONHCH_2(CF_2)_8CH_2NHCOC_6H_{11}$.

M. P. 70–72° C.

Example 7

In the same manner as in Example 1 except that 3,6,9-oxydecanecarboxylyl chloride (1.2 moles) was used in place of lauryl chloride, the reaction was carried out to obtain a triblock compound 7 of the formula:

$CH_3CH_2O(CH_2CH_2O)_2CH_2CONHCH_2(CF_2)_8CH_2NHCOCH_2—(OCH_2CH_2)_2OCH_2CH_3$.

B. P. 230–232° C./0.08 mmHg.

Example 8

In toluene (800 g), 1H,1H,10H,10H-perfluoro-1,10-decanediol (0.5 mole), stearyl bromide (1 mole) and pyridine (0.5 moles) were reacted at 130° C. for 6 hours. After cooling, the reaction mixture was diluted by water, and an organic layer was separated, washed with an aqueous solution of sodium hydrogen carbonate, and dried over magnesium sulfate, followed by evaporation off of the solvent. The residue was purified by recrystallization or distillation to obtain a triblock compound 8 of the formula:

$CH_3(CH_2)_{17}OCH_2(CF_2)_8CH_2O(CH_2)_{17}CH_3$.

M. P. 49–51° C.

Example 9

In toluene (800 g), 1H,1H,10H,10H-perfluoro-1,10-decanediol (0.5 mole) and stearyl isocyanate (1 mole) were reacted at 80° C. for 6 hours. After cooling, the reaction product was purified by recrystallization or distillation to obtain a triblock compound 9 of the formula:

$CH_3(CH_2)_{17}NHCOOCH_2(CF_2)_8CH_2OCONH(CH_2)_{17}CH_3$.

M. P. 109–110° C.

Example 10

In toluene (800 g), 1H,1H,10H,10H-perfluoro-1,10-decanediamine (0.5 mole) and stearyl isocyanate (1 mole) were reacted at 80° C. for 6 hours. After cooling, the reaction product was purified by recrystallization or distillation to obtain a triblock compound 10 of the formula:

$CH_3(CH_2)_{17}NHCONHCH_2(CF_2)_8CH_2NHCONH(CH_2)_{17}CH_3$.

M. P. 110–112° C.

Example 11

In isopropanol (800 g), 1H,1H,10H,10H-perfluoro-1,10-decanedicarboxylic acid (0.5 mole) and stearylamine (1 mole) were reacted at 130° C. for 6 hours. After cooling, the reaction product was purified by recrystallization or distillation to obtain a triblock compound 11 of the formula:.

$CH_3(CH_2)_{17}NH_3^{+-}OCOCH_2(CF_2)_8CH_2COO^{-+}H_3N(CH_2)_{17}CH_3$.

M. P. 60–62° C.

Example 12

In toluene (800 g), 1H,H,10H, 10H-perfluorodecane-1,10-diglycidyl ether (0.5 mole) and stearyl alcohol (1 mole) were reacted in the presence of tin tetrachloride (0.02 mole) at 100° C. for 6 hours. After cooling, the reaction product was purified by recrystallization or distillation to obtain a triblock compound 12 of the formula:

$CH_3(CH_2)_{17}OCH_2CH(OH)CH_2OCH_2(CF_2)_8CH_2OCH_2CH(OH)—CH_2O(CH_2)_{17}CH_3$.

M. P. 70–72° C.

Example 13

In toluene (800 g), 1H,1H,18H,18H-perfluoro-1,18-octadecanediamine (0.5 mole), stearyl chloride (1.2 moles) and pyridine (0.5 mole) were reacted at 100° C. for 6 hours. After cooling, the reaction mixture was diluted by water, and an organic layer was separated, washed with an aqueous solution of sodium hydrogen carbonate, and dried over magnesium sulfate, followed by evaporation off of the solvent. The residue was purified by recrystallization or distillation to obtain a triblock compound 13 of the formula:

$CH_3(CH_2)_{16}CONHCH_2(CF_2)_{16}CH_2NHCO(CH_2)_{16}CH_3$.

M. P. 130–132° C.

Example 14

In toluene (800 g), 1H,1H,18H,18H-perfluoro-1,18-octadecanediol (0.5 mole), stearyl bromide (1 mole) and pyridine (0.5 mole) were reacted at 130° C. for 6 hours. After cooling, the reaction mixture was diluted by water, and an organic layer was separated, washed with an aqueous solution of sodium hydrogen carbonate, and dried over magnesium sulfate, followed by evaporation off of the solvent. The residue was purified by recrystallization or distillation to obtain a triblock compound 14 of the formula:

$CH_3(CH_2)_{17}OCH_2(CF_2)_{16}CH_2O(CH_2)_{17}CH_3$.

M. P. 53–55° C.

Example 15

In isopropanol (800 g), 1 H,1 H,18H,18H-perfluoro-1,18-octadecanedicarboxylic acid (0.5 mole) and stearylamine (1 mole) were reacted at 130° C. for 6 hours. After cooling, the reaction product was purified by recrystallization or distillation to obtain a triblock compound 15 of the formula:

$CH_3(CH_2)_{17}NH_3OCOCH_2(CF_2)_{16}CH_2COOH_3N(CH_2)_{17}CH_3$.

M. P. 97–99° C.

Example 16

In toluene (800 g), 1H, 1H,18H,18H-perfluoro-1,18-octadecanediol (0.5 mole) and stearyl isocyanate (1 mole) were reacted at 80° C. for 6 hours. After cooling, the reaction product was purified by recrystallization or distillation to obtain a triblock compound 16 of the formula:

$CH_3(CH_2)_{17}NHCOOCH_2(CF_2)_{16}CH_2OCONH(CH_2)_{17}CH_3$.

M. P. 128–129° C.

Example 17

In toluene (800 g), 1H,1H,18H,18H-perfluoro-1,18-octadecanediamine (0.5 mole) and stearyl isocyanate (1 mole) were reacted at 80° C. for 6 hours. After cooling, the reaction product was purified by recrystallization or distillation to obtain a triblock compound 15 of the formula:

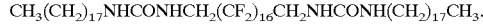

$CH_3(CH_2)_{17}NHCONHCH_2(CF_2)_{16}CH_2NHCONH(CH_2)_{17}CH_3$.

M. P. 126–128
Formation of magnetic layer and protective layer

Example 18

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $SiO_r$ protective layer having a thickness of 200 Å was formed by a plasma polymerization using a FR power source of 13.56 MHz and 1 kW with supplying $SiH_4$ at 20 ml/min., oxygen at 40 ml/min., helium at 150 ml/min. and hydrogen at 30 ml/min.

Example 19

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a diamond-like carbon protective layer having a thickness of 200 Å was formed by a plasma polymerization using a FR power source of 13.56 MHz and 1 kW with supplying $C_2H_4$ at 60 ml/min. and hydrogen at 120 ml/min.

Example 20

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $AlO_s$ protective layer having a thickness of 200 Å was formed by a plasma polymerization using a FR power source of 50 kHz and 1 kW with supplying $Al(OC_2H_5)_3$ at 60 ml/min., oxygen at 90 ml/min., helium at 150 ml/min. and hydrogen at 30 ml/min.

Example 21

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $TiO_r$ protective layer having a thickness of 200 Å was formed by a plasma polymerization using a FR power source of 50 kHz and 1 kW with supplying $Ti(OC_2H_5)_4$ at 60 ml/min., oxygen at 120 ml/min., helium at 150 ml/min. and hydrogen at 30 ml/min.

Example 22

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $SiC_p$ protective layer having a thickness of 200 Å was formed by a plasma polymerization using a FR power source of 13.56 MHz and 1 kW with supplying $C_2H_4$ at 30 ml/min., $SiH_4$ at 30 ml/min., helium at 150 ml/min. and hydrogen at 30 ml/min.

Example 23

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $B_qC$ protective layer having a thickness of 200 Å was formed by a plasma polymerization using a FR power source of 13.56 MHz and 1 kW with supplying $C_2H_4$ at 20 ml/min., $B_2H_6$ at 80 ml/min., helium at 150 ml/min. and hydrogen at 30 ml/min.

Example 24

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $ZrO_r$ protective layer having a thickness of 200 Å was formed by a plasma polymerization using a FR power source of 50 kHz and 1 kW with supplying $Zr(OC_2H_5)_4$ at 50 ml/min., oxygen at 75 ml/min., helium at 150 ml/min. and hydrogen at 30 ml/min.

Example 25

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $BN_q$ protective layer having a thickness of 200 Å was formed by a plasma polymerization using a FR power source of 13.56 MHz and 1 kW with supplying $B_2H_6$ at 80 ml/min., nitrogen at 160 ml and hydrogen at 30 ml/min.

Example 26

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $SiN_q$ protective layer having a thickness of 200 Å was formed by a plasma polymerization using a FR power source of 13.56 MHz and 1 kW with supplying $SiH_4$ at 60 ml/min. nitrogen at 160 ml/min. and hydrogen at 30 ml/min.

Example 27

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a $CN_q$ protective layer having a thickness of 200 Å was formed by a plasma polymerization using a FR power source of 13.56 MHz and 1 kW with supplying $C_2H_4$ at 20 ml/min., nitrogen at 100 ml/min. and hydrogen at 30 ml/min.

Example 28

On a polyolefin disc substrate having a thickness of 1.2 mm and a diameter of 2.5 inches, a chromium primer layer having a thickness of 0.1 μm and a Co—Cr—P magnetic layer having a thickness of 0.03 μm were successively formed by sputtering. Thereafter, on the magnetic layer, a diamond-like carbon protective layer having a thickness of 200 Å was formed by a plasma polymerization using a FR power source of 13.56 MHz and 1 kW with supplying $C_2H_4$ at 60 ml/min. and hydrogen at 120 ml/min.

Example 29

On a polyolefin disc substrate having a thickness of 1.2 mm and a diameter of 2.5 inches, a chromium primer layer having a thickness of 0.1 μm and a Co—Cr—P magnetic layer having a thickness of 0.03 μm were successively formed by sputtering. Thereafter, on the magnetic layer, a $SiO_r$ protective layer having a thickness of 200 Å was formed by a plasma polymerization using a FR power source of 13.56 MHz and 1 kW with supplying $SiH_4$ at 20 ml/min., oxygen at 40 ml/min., helium at 150 ml/min. and hydrogen at 30 ml/min.

Example 30

On a polyolefin disc substrate having a thickness of 0.8 mm and a diameter of 2.5 inches, a chromium primer layer having a thickness of 0.1 μm and a Co—Cr—P magnetic layer having a thickness of 0.03 μm were successively formed by sputtering. Thereafter, on the magnetic layer, a $ZrO_r$ protective layer having a thickness of 200 Å was formed by a plasma polymerization using a FR power source of 50 kHz and 1 kW with supplying $Zr(OC_2H_5)_4$ at 50 ml/min., oxygen at 75 ml/min., helium at 150 ml/min. and $H_2$ at 30 ml/min.

Example 31

On a polycarbonate disc substrate having a thickness of 1.2 mm and a diameter of 2.5 inches, a $SiN_x$ enhancing layer having a thickness of 0.08 μm, a Tb—Fe—Co magnetic layer having a thickness of 0.03 μm, a $SiN_x$ enhancing layer having a thickness of 0.02 μm and an aluminum alloy reflecting layer having a thickness of 0.05 μm were successively formed by sputtering. Then, on the reflecting layer, a UV-light curable resin layer having a thickness of 10 μm was coated and cured by the irradiation of UV light. Thereafter, on the cured resin layer, a diamond-like carbon protective layer having a thickness of 300 Å was formed by a plasma polymerization using a FR power source of 13.56 MHz and 1 kW with supplying $C_2H_4$ at 60 ml/min. and hydrogen at 120 ml/min.

Example 32

On a polycarbonate disc substrate having a thickness of 1.2 mm and a diameter of 2.5 inches, a $SiN_x$ enhancing layer having a thickness of 0.08 μm, a Tb—Fe—Co magnetic layer having a thickness of 0.03 μm, a $SiN_x$ enhancing layer having a thickness of 0.02 μm and an aluminum alloy reflecting layer having a thickness of 0.05 μm were successively formed by sputtering. Then, on the reflecting layer, a UV-light curable resin layer having a thickness of 10 μm was coated and cured by the irradiation of UV light. Thereafter, on the cured resin layer, a $SiO_r$ protective layer having a thickness of 300 Å was formed by a plasma polymerization using a FR power source of 13.56 MHz and 1 kW with supplying $SiH_4$ at 20 ml/min., oxygen at 40 ml/min., helium at 150 ml/min. and hydrogen at 30 ml/min.

Example 33

On an aluminum alloy disc substrate having a thickness of 1.2 mm and a diameter of 2.5 inches which carried a Ni—P plated layer having a thickness of 15 μm on its surface, a FeNi (Permalloy) layer having a thickness of 0.2 μm, a titanium layer having a thickness of 0.1 μm and a Co—Cr magnetic layer having a thickness of 0.05 μm were successively formed by sputtering. Thereafter, on the magnetic layer, a diamond-like carbon protective layer having a thickness of 200 Å was formed by a plasma polymerization using a FR power source of 13.56 MHz and 1 kW with supplying $C_2H_4$ at 60 ml/min. and hydrogen at 120 ml/min.

Example 34

On an aluminum alloy disc substrate having a thickness of 0.8 mm and a diameter of 2.5 inches which carried a Ni—P plated layer having a thickness of 15 μm on its surface, a FeNi (Permalloy) layer having a thickness of 0.2 μm, a titanium layer having a thickness of 0.1 μm and a Co—Cr magnetic layer having a thickness of 0.05 μm were successively formed by sputtering. Thereafter, on the magnetic layer, a $SiO_r$ protective layer having a thickness of 200 Å was formed by a plasma polymerization using a FR power source of 13.56 MHz and 1 kW with supplying $SiH_4$ at 20 ml/min., oxygen at 40 ml/min., helium at 150 ml/min. and hydrogen at 30 ml/min.

Example 35

On an aluminum alloy disc substrate having a thickness of 0.8 mm and a diameter of 2.5 inches which carried a Ni—P plated layer having a thickness of 15 μm on its surface, a chromium primer layer having a thickness of 0.1 μm and a Co—Cr—Pt magnetic layer having a thickness of 0.03 μm were successively formed by sputtering. Thereafter, on the magnetic layer, a diamond-like carbon protective layer having a thickness of 200 Å was formed by a plasma polymerization using a FR power source of 13.56 MHz and 1 kW with supplying $C_2H_4$ at 60 ml/min. and hydrogen at 120 ml/min.

Example 36

On an aluminum alloy disc substrate having a thickness of 0.8 mm and a diameter of 2.5 inches which carried a Ni—P plated layer having a thickness of 15 μm on its surface, a chromium primer layer having a thickness of 0.1 μm and a Co—Cr—Pt magnetic layer having a thickness of 0.03 μm were successively formed by sputtering. Thereafter, on the magnetic layer, a $SiO_r$ protective layer having a thickness of 200 Å was formed by a plasma polymerization using a FR power source of 13.56 MHz and 1 kW with supplying $SiH_4$ at 20 ml/min., oxygen at 40 ml/min., helium at 150 ml/min. and hydrogen at 30 ml/min.

Example 37

On an aluminum alloy disc substrate having a thickness of 0.8 mm and a diameter of 2.5 inches which carried a Ni—P plated layer having a thickness of 15 μm on its surface, a chromium primer layer having a thickness of 0.1 μm and a Co—Cr—Pt magnetic layer having a thickness of 0.03 μm were successively formed by sputtering. Thereafter, on the magnetic layer, a $ZrO_r$ protective layer having a thickness of 200 Å was formed by a plasma polymerization using a FR power source of 13.56 MHz and 1 kW with supplying $Zr(OC_2H_5)$ at 50 ml/min., oxygen at 75 ml/min., helium at 150 ml/min. and hydrogen at 30 ml/min.

Example 38

On a polycarbonate disc substrate having a thickness of 1.2 mm and a diameter of 2.5 inches, a $SiN_x$ enhancing layer having a thickness of 0.08 μm, a Tb—Fe—Co magnetic layer having a thickness of 0.03 μm, a $SiN_x$ enhancing layer having a thickness of 0.02 μm and an aluminum alloy reflecting layer having a thickness of 0.05 μm were successively formed by sputtering. Then, on the reflecting layer, a UV-light curable resin layer having a thickness of 10 μm was coated and cured by the irradiation of UV light. Thereafter, on the cured resin layer, a Si—O—C protective layer having a thickness of 200 Å was formed by a plasma polymerization using a FR power source of 50 kHz and 1 kW with supplying $(CH_3)_3Si$—O—Si—$(CH_3)_3$ at 20 ml/min., oxygen at 40 ml/min., helium at 150 ml/min. and hydrogen at 30 ml/min.

Example 39

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a Si—O—C protective layer having a thickness of 200 Å was formed by a plasma polymerization using a FR power source of 50 kHz and 1 kW with supplying $(CH_3)_3Si$—O—Si—$(CH_3)_3$ at 20 ml/min., oxygen at 40 ml/min., helium at 150 ml/min. and hydrogen at 30 ml/min.

Preparation of lubricant solution

Example 40

Solubility of each of the compounds obtained in Examples 1–17 in general solvents was checked using n-hexane, cyclohexane and toluene.

At room temperature, 3 g of each compound was added to 97 g of each of n-hexane, cyclohexane and toluene and stirred with a glass rod for 5 minutes. All the compounds were completely dissolved in n-hexane, cyclohexane and toluene, and all the obtained lubricant solutions were colorless and transparent.

Formation of lubricant layer and measurement of sliding movement property

Example 41

Each of the magnetic media produced in Examples 18–27 and 39 was cut at a width of 8 mm, and dipped in a 0.2 wt. % solution of each of the compounds obtained in Examples 1–17 in n-hexane for 30 seconds and pulled up, followed by drying with warm air to form a lubricant layer on the surface of each magnetic medium.

Each sample of the magnetic tape was set around a cylinder for an 8 mm tape having a diameter of 4 cm at a winding angle of 220 degrees. Then, a sine wave having a wavelength of 1.6 μm was recorded on the magnetic tape sample at a relative speed between the magnetic tape sample and a magnetic head of 11.3 m/sec. under a tension of 12.5 gf/cm, and a reproducing output in a still mode and a load on the cylinder in the still state were measured.

A still life is a time at which the reproducing output decreases by 6 dB from the original reproducing output. As the load on the cylinder, a voltage which is outputted on a voltmeter in the still state.

Comparative Example 1

Each of the magnetic media produced in Examples 18–27 and 39 was cut at a width of 8 mm, and dipped in a 0.2 wt. % solution of a perfluoropolyether liquid lubricant Fomblin (trademark) Z-DOL $(HOCH_2O(CF_2O)_{10}(C_2F_4O)_{10}CH_2OH)$ in perfluoro-octane for 30 seconds and pulled up, followed by drying with warm air to form a lubricant layer on the surface of each magnetic medium.

Then, a still life and a load on the cylinder were measured in the same manners as in Example 41 except that a tension during the recording was changed to 10 gf/cm.

Comparative Example 2

Each of the magnetic media produced in Examples 18–27 and 39 was cut at a width of 8 mm, and dipped in a 0.2 wt. % solution of a perfluoropolyether liquid lubricant Fomblin (trademark) Z-AM 2001 $(H_2CO_2C_6H_3OCH_2O(CF_2O)_{10}(C_2F_4O)_{10}CH_2O$—$C_6H_3O_2CH_2)$ in perfluorooctane for 30 seconds and pulled up, followed by drying with warm air to form a lubricant layer on the surface of each magnetic medium.

Then, a still life and a load on the cylinder were measured in the same manners as in Example 41 except that a tension during the recording was changed to 10 gf/cm.

The results obtained in Example 41 and Comparative Examples 1 and 2 are shown in Table 1.

TABLE 1

| Magnetic medium | Lubricant compound | Still life (min.) | Load on cylinder (mV) |
|---|---|---|---|
| Examples 18–27 | Example 1 | >600 | 43–46 |
| Example 39 | Example 1 | >600 | 43–45 |
| Examples 18–27 | Example 2 | >600 | 41–44 |
| Example 39 | Example 2 | >600 | 42–44 |
| Examples 18–27 | Example 3 | >600 | 42–45 |
| Example 39 | Example 3 | >600 | 43–45 |
| Examples 18–27 | Example 4 | >600 | 41–44 |
| Example 39 | Example 4 | >600 | 42–44 |
| Examples 18–27 | Example 5 | >600 | 42–44 |
| Example 39 | Example 5 | >600 | 43–45 |
| Examples 18–27 | Example 6 | >600 | 40–44 |
| Example 39 | Example 6 | >600 | 41–44 |
| Examples 18–27 | Example 7 | >600 | 42–44 |
| Example 39 | Example 7 | >600 | 42–46 |
| Examples 18–27 | Example 8 | >600 | 42–44 |
| Example 39 | Example 8 | >600 | 42–44 |
| Examples 18–27 | Example 9 | >600 | 42–43 |
| Example 39 | Example 9 | >600 | 42–43 |
| Examples 18–27 | Example 10 | >600 | 40–42 |
| Example 39 | Example 10 | >600 | 40–44 |
| Examples 18–27 | Example 11 | >600 | 40–42 |
| Example 39 | Example 11 | >600 | 42–44 |
| Examples 18–27 | Example 12 | >600 | 40–42 |
| Example 39 | Example 12 | >600 | 40–42 |
| Examples 18–27 | Example 13 | >600 | 42–45 |
| Example 39 | Example 13 | >600 | 43–45 |
| Examples 18–27 | Example 14 | >600 | 40–42 |
| Example 39 | Example 14 | >600 | 40–42 |
| Examples 18–27 | Example 15 | >600 | 43–45 |
| Example 39 | Example 15 | >600 | 43–45 |
| Examples 18–27 | Example 16 | >600 | 45–48 |
| Example 39 | Example 16 | >600 | 45–50 |
| Examples 18–27 | Example 17 | >600 | 46–50 |
| Example 39 | Example 17 | >600 | 45–50 |
| Examples 18–27 | Comp. Ex. 1 | 35 | 65–75 |
| Example 39 | Comp. Ex. 1 | 35 | 65–73 |
| Examples 18–27 | Comp. Ex. 2 | 55 | 65–70 |
| Example 39 | Comp. Ex. 2 | 55 | 62–70 |

From the results in Table 1, when the lubricants of the present invention were used, the good still life of longer than 600 minutes was achieved. The lubricants of the present invention achieved the load on the cylinder in the still state which was smaller by about 25% than the conventional perfluoropolyether lubricants (Fomblin), whereby the still life is improved, and an amount of consumed electric power of a motor is reduced.

CSS durability test

Example 42

On each of the magnetic discs produced in Examples 28–30 and 33–37, a 0.2 wt. % solution of each of the compounds obtained in Examples 1–17 in n-hexane was spin coated.

Each magnetic disc was set in a disc drive which rotated the disc at 5400 rpm and a linear speed of 10 m/sec. in a normal state, and subjected to the CSS (contact/start/stop) durability test using a magnetic head slider. As a CSS life, the number of cycles till a coefficient of friction abruptly increased when the disc was started was used.

Comparative Example 3

On each of the magnetic discs produced in Examples 28–30 and 33–37, a 0.2 wt. % solution of a perfluoropolyether liquid lubricant Fomblin (trademark) Z-DOL ($HOCH_2O(CF_2O)_{10}(C_2F_4O)_{10}-CH_2OH$) in perfluorooctane was spin coated.

Then, each magnetic disc was subjected to the CSS durability test in the same manner as in Example 42.

Comparative Example 4

On each of the magnetic discs produced in Examples 28–30 and 33–37, a 0.2 wt. % solution of a perfluoropolyether liquid lubricant Fomblin (trademark) Z-AM 2001 ($H_2CO_2C_6H_3OCH_2O(CF_2O)_{10}-(C_2F_4O)_{10}CH_2OC_6H_3O_2CH_2$) in perfluorooctane was spin coated.

Then, each magnetic disc was subjected to the CSS durability test in the same manner as in Example 42.

The results in the above CSS test are shown in Table 2.

TABLE 2

| Magnetic disc | Lubricant | CSS life (cycles) | Coefficient of friction |
|---|---|---|---|
| Examples 28–30 | Example 1 | >100,000 | 0.25 |
| Examples 33–37 | Example 1 | >100,000 | 0.26 |
| Examples 28–30 | Example 2 | >100,000 | 0.23 |
| Examples 33–37 | Example 2 | >100,000 | 0.25 |
| Examples 28–30 | Example 3 | >100,000 | 0.25 |
| Examples 33–37 | Example 3 | >100,000 | 0.24 |
| Examples 28–30 | Example 4 | >100,000 | 0.23 |
| Examples 33–37 | Example 4 | >100,000 | 0.24 |
| Examples 28–30 | Example 5 | >100,000 | 0.25 |
| Examples 33–37 | Example 5 | >100,000 | 0.23 |
| Examples 28–30 | Example 6 | >100,000 | 0.23 |
| Examples 33–37 | Example 6 | >100,000 | 0.23 |
| Examples 28–30 | Example 7 | >100,000 | 0.24 |
| Examples 33–37 | Example 7 | >100,000 | 0.24 |
| Examples 28–30 | Example 8 | >100,000 | 0.23 |
| Examples 33–37 | Example 8 | >100,000 | 0.23 |
| Examples 28–30 | Example 9 | >100,000 | 0.23 |
| Examples 33–37 | Example 9 | >100,000 | 0.22 |
| Examples 28–30 | Example 10 | >100,000 | 0.21 |
| Examples 33–37 | Example 10 | >100,000 | 0.20 |
| Examples 28–30 | Example 11 | >100,000 | 0.20 |
| Examples 33–37 | Example 11 | >100,000 | 0.22 |
| Examples 28–30 | Example 12 | >100,000 | 0.20 |
| Examples 33–37 | Example 12 | >100,000 | 0.23 |
| Examples 28–30 | Example 13 | >100,000 | 0.25 |
| Examples 33–37 | Example 13 | >100,000 | 0.25 |
| Examples 28–30 | Example 14 | >100,000 | 0.20 |
| Examples 33–37 | Example 14 | >100,000 | 0.20 |
| Examples 28–30 | Example 15 | >100,000 | 0.25 |
| Examples 33–37 | Example 15 | >100,000 | 0.25 |
| Examples 28–30 | Example 16 | >100,000 | 0.24 |
| Examples 33–37 | Example 16 | >100,000 | 0.25 |
| Examples 28–30 | Example 17 | >100,000 | 0.24 |
| Examples 33–37 | Example 17 | >100,000 | 0.25 |
| Examples 28–30 | Comp. Ex. 3 | 25,000 | 0.32 |
| Examples 33–37 | Comp. Ex. 3 | 30,000 | 0.30 |
| Examples 28–30 | Comp. Ex. 4 | 30,000 | 0.30 |
| Examples 33–37 | Comp. Ex. 4 | 32,000 | 0.29 |

As seen from the results in Table 2, the lubricants of the present invention achieved the CSS life of more than 100,000 cycles, and their coefficients of friction were from 0.20 to 0.25, which were much smaller than the coefficients of friction of the conventional perfluoropolyether liquid lubricants.

Example 43

On each of the MO discs produced in Examples 31, 32, and 38, a 0.2 wt. % solution of each of the compounds obtained in Examples 1–17 in n-hexane was spin coated.

Each disc was set in a disc drive and subjected to a durability test using a plastic slider at 600 rpm and a linear speed of 1.2 m/sec. The durability was expressed by the number of rotations till a coefficient of friction abruptly increased.

Comparative Example 5

On each of the MO discs produced in Examples 31, 32 and 38, a 0.2 wt. % solution of a perfluoropolyether liquid lubricant Fomblin (trademark) Z-DOL ($HOCH_2O(CF_2O)_{10}(C_2F_4O)_{10}CH_2OH$) in perfluorooctane was spin coated.

Then, each magnetic disc was subjected to the durability test in the same manner as in Example 43.

Comparative Example 6

On each of the magnetic discs produced in Examples 31, 32 and 38, a 0.2 wt. % solution of a perfluoropolyether liquid lubricant Fomblin (trademark) Z-AM 2001 ($H_2CO_2C_6H_3OCH_2O(CF_2O)_{10}-(C_2F_4O)_{10}CH_2OC_6H_3O_2CH_2$) in perfluorooctane was spin coated.

Then, each magnetic disc was subjected to the durability test in the same manner as in Example 43.

The results in the above CSS tit are shown in Table 3.

TABLE 3

| Magnetic disc | Lubricant | Durability (rotations) | Coefficient of friction |
|---|---|---|---|
| Examples 31–32 | Example 1 | >300,000 | 0.24 |
| Example 38 | Example 1 | >300,000 | 0.22 |
| Examples 31–32 | Example 2 | >300,000 | 0.20 |
| Example 38 | Example 2 | >300,000 | 0.22 |
| Examples 31–32 | Example 3 | >300,000 | 0.24 |
| Example 38 | Example 3 | >300,000 | 0.22 |
| Examples 31–32 | Example 4 | >300,000 | 0.20 |
| Example 38 | Example 4 | >300,000 | 0.22 |
| Examples 31–32 | Example 5 | >300,000 | 0.22 |
| Example 38 | Example 5 | >300,000 | 0.22 |
| Examples 31–32 | Example 6 | >300,000 | 0.20 |
| Example 38 | Example 6 | >300,000 | 0.18 |
| Examples 31–32 | Example 7 | >300,000 | 0.20 |
| Example 38 | Example 7 | >300,000 | 0.18 |
| Examples 31–32 | Example 8 | >300,000 | 0.20 |
| Example 38 | Example 8 | >300,000 | 0.20 |
| Examples 31–32 | Example 9 | >300,000 | 0.20 |
| Example 38 | Example 9 | >300,000 | 0.18 |
| Examples 31–32 | Example 10 | >300,000 | 0.20 |
| Example 38 | Example 10 | >300,000 | 0.18 |
| Examples 31–32 | Example 11 | >300,000 | 0.17 |
| Example 38 | Example 11 | >300,000 | 0.20 |
| Examples 31–32 | Example 12 | >300,000 | 0.20 |
| Example 38 | Example 12 | >300,000 | 0.18 |
| Examples 31–32 | Example 13 | >300,000 | 0.18 |
| Example 38 | Example 13 | >300,000 | 0.20 |
| Examples 31–32 | Example 14 | >300,000 | 0.17 |
| Example 38 | Example 14 | >300,000 | 0.17 |
| Examples 31–32 | Example 15 | >300,000 | 0.22 |
| Example 38 | Example 15 | >300,000 | 0.24 |
| Examples 31–32 | Example 16 | >300,000 | 0.18 |
| Example 38 | Example 16 | >300,000 | 0.20 |
| Examples 31–32 | Example 17 | >300,000 | 0.18 |
| Example 38 | Example 17 | >300,000 | 0.18 |
| Examples 31–32 | Comp. Ex. 5 | 9,000 | 0.32 |
| Example 38 | Comp. Ex. 5 | 8,500 | 0.30 |
| Examples 31–32 | Comp. Ex. 6 | 9,500 | 0.32 |
| Example 38 | Comp. Ex. 6 | 9,200 | 0.29 |

As seen from the results in Table 3, the lubricants of the present invention achieved the durability of more than 300,000 rotations, and their coefficients of friction during the disc rotation were smaller than the coefficients of friction of the conventional perfluoropolyether liquid lubricants.

Example 44

α-iron magnetic powder (coercive force of 1500 Oe and saturation magnetization of 120 emu/g) (100 wt. parts), a vinyl chloride-vinyl acetate-vinyl alcohol copolymer (VAGH manufactured by UCC) (20 wt. parts), a polyfunctional isocyanate compound (5 wt. parts), carbon black (3 wt. parts), α—$Al_2O_3$ (3 wt. parts), myristic acid (2 wt. parts), the compound prepared in Example 2, 8, 9, 10 or 11 (3 wt. parts), cyclohexanone (150 wt. parts) and toluene (130 wt. parts) were mixed in a ball mill for 72 hours to obtain a magnetic paint.

On an aramide film having a thickness of 4 μm, the prepared magnetic paint was coated to a thickness of 0.5 μm, calendered and cut to a width of 8 mm to obtain a coating type magnetic tape.

The magnetic tape was set around a cylinder for an 8 mm tape having a diameter of 4 cm at a winding angle of 220 degrees. Then, a sine wave having a wavelength of 1.6 μm was recorded on the magnetic tape sample at a relative speed between the magnetic tape sample and a magnetic head of 11.3 m/sec. under a tension of 10 gf/cm, and a reproducing output in a still mode and a load on the cylinder in the still state were measured.

A still life is a time at which the reproducing output decreases by 6 dB from the original reproducing output. As the load on the cylinder, a voltage which is outputted on a voltmeter in the still state.

Comparative Example 7

In the same manner as in Example 44 except that any compound produced in Example 2, 8, 9, 10 or 11 was not used, and myristic acid (2 wt. parts) was used as a lubricant, a magnetic tape was produced and subjected to the same measurements of the still life and the load on the cylinder.

The results in Example 44 and Comparative Example 7 are shown in Table 4.

TABLE 4

| Lubricant  | Still life (min) | Load on cylinder (mV) |
|------------|------------------|------------------------|
| Example 2  | >600             | 45–47                  |
| Example 8  | >600             | 43–46                  |
| Example 9  | >600             | 42–45                  |
| Example 10 | >600             | 40–45                  |
| Example 11 | >600             | 45–47                  |
| Comp. Ex. 7| 55               | 65–67                  |

As seen from the results in Table 4, when the lubricant comprising the compound (1) of the present invention was used, the durability was longer than 600 minutes, and the load on the cylinder was much smaller than when the conventional lubricant comprising myristic acid was used.

Example 45

α-Iron magnetic powder (coercive force of 1500 Oe and saturation magnetization of 120 emu/g) (100 wt. parts), a vinyl chloride-vinyl acetate-vinyl alcohol copolymer (VAGH manufactured by UCC) (20 wt. parts), a polyfunctional isocyanate compound (5 wt. parts), carbon black (3 wt. parts), α—$Al_2O_3$ (3 wt. parts), myristic acid (2 wt. parts), cyclohexanone (150 wt. parts) and toluene (130 wt. parts) were mixed in a ball mill for 72 hours to obtain a magnetic paint.

On an aramide film having a thickness of 4 μm, the prepared magnetic paint was coated to a thickness of 0.5 μm to form a magnetic layer, and the film was dipped in a 0.1 wt. % solution of the compound prepared in Example 2, 8, 9, 10 or 11 in n-hexane and pulled up following by drying to form a solid lubricant layer. After calendering, the film was cut to a width of 8 mm to obtain a coating type magnetic tape.

The magnetic tape was set around a cylinder for an 8 mm tape having a diameter of 4 cm at a winding angle of 220 degrees. Then, a sine wave having a wavelength of 1.6 μm was recorded on the magnetic tape sample at a relative speed between the magnetic tape sample and a magnetic head of 11.3 m/sec. under a tension of 10 gf/cm, and a reproducing output in a still mode and a load on the cylinder in the still state were measured.

A still life is a time at which the reproducing output decreases by 6 dB from the original reproducing output. As the load on the cylinder, a voltage which is outputted on a voltmeter in the still state is used.

Comparative Example 8

In the same manner as in Example 45 except that a 0.1 wt. % solution of myristic acid was used in place of the solution of the compound produced in Example 2, 8, 9, 10 or 11, a magnetic tape was produced and subjected to the same measurements of the still life and the load on the cylinder.

The results in Example 45 and Comparative Example 8 are shown in Table 5.

TABLE 5

| Lubricant  | Still life (min) | Load on cylinder (mV) |
|------------|------------------|------------------------|
| Example 2  | >600             | 45–47                  |
| Example 8  | >600             | 40–46                  |
| Example 9  | >600             | 42–46                  |
| Example 10 | >600             | 40–42                  |
| Example 11 | >600             | 45–48                  |
| Comp. Ex. 7| 55               | 65–67                  |

As seen from the results of Table 5, when the lubricant comprising the compound of the formula (1) according to the present invention was coated on the surface of the coating type magnetic recording medium, the still life was longer than 600 minutes, and the load on cylinder in the still state was much smaller than when myristic acid, which is one of the conventional lubricant, was coated.

Formation of Si—M—O protective film

Example 46

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a Si—C—O protective layer having a thickness of 200 Å was formed by using a FR power source of 13.56 MHz and 1 kW with supplying $(CH_3O)_3Si$—O—$Si(OCH_3)_3$ at 20 ml/min., oxygen at 40 ml/min., hydrogen at 20 ml/min. and helium at 80 ml/min.

Example 47

On a polyethylene terephthalate film having a thickness of 6.3 μm, cobalt was obliquely deposited in an oxygen atmosphere to form a cobalt oxide layer of 0.15 μm in thickness.

Thereafter, on the cobalt oxide layer, a Si—C—O protective layer having a thickness of 200 Å was formed by using a FR power source of 13.56 MHz and 1 kW with supplying SiH$_4$ at 20 ml/min., C$_2$H$_4$ at 4 ml/min., oxygen at 40 ml/min., hydrogen at 20 ml/min. and helium at 80 ml/min.

Example 48

On a polyethylene terephthalate film having a thickness of 6.3 μm, cobalt was obliquely deposited in an oxygen atmosphere to form a cobalt oxide layer of 0.15 μm in thickness. Thereafter, on the cobalt oxide layer, a Si—C—O protective layer having a thickness of 200 Å was formed by using a FR power source of 13.56 MHz and 1 kW and a microwave of 2.45 GHz and 1.5 kW with supplying SiH$_4$ at 20 ml/min., C$_2$H$_4$ at 4 ml/min., oxygen at 40 ml/min., hydrogen at 20 ml/min. and helium at 80 ml/min.

Example 49

On a polyethylene naphthalate film having a thickness of 4 μm, cobalt was obliquely deposited in an oxygen atmosphere to form a cobalt oxide layer of 0.15 μm in thickness. Thereafter, on the cobalt oxide layer, a Si—C—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min.

Example 50

On an aramide film having a thickness of 4 μm, cobalt was obliquely deposited in an oxygen atmosphere to form a cobalt oxide layer of 0.15 μm in thickness. Thereafter, on the cobalt oxide layer, a Si—C—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min.

Example 51

On a polyethylene naphthalate film having a thickness of 4 μm, cobalt was obliquely deposited in an oxygen atmosphere to form a cobalt oxide layer of 0.15 μm in thickness. Thereafter, on the cobalt oxide layer, a Si—N—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., nitrogen at 10 ml/min., hydrogen at 20 ml/min. and helium at 80 ml/min.

Example 52

On a polyethylene naphthalate film having a thickness of 4 μm, cobalt was obliquely deposited in an oxygen atmosphere to form a cobalt oxide layer of 0.15 μm in thickness. Thereafter, a Si—B—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., B$_2$H$_6$ at 10 ml/min., hydrogen at 20 ml/min. and helium at 80 ml/min.

Example 53

On a polyethylene terephthalate film having a thickness of 6.3 μm, a Si—C—O primer layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min. On the primer layer, cobalt was obliquely deposited in an oxygen atmosphere to form a cobalt oxide layer of 0.15 μm in thickness. Thereafter, a Si—C—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min.

Example 54

On a polyethylene naphthalate film having a thickness of 4 μm, a Si—C—O primer layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min. On the primer layer, cobalt was obliquely deposited in an oxygen atmosphere to form a cobalt oxide layer of 0.15 μm in thickness. Thereafter, a Si—C—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min.

Example 55

On an aramide film having a thickness of 4 μm, a Si—C—O primer layer having a thickness of 200 Å was formed by using a FR power source of 13.56 MHz and 1 kW with supplying (CH$_3$O)$_3$Si—O— Si(OCH$_3$)$_3$ at 20 ml/min., oxygen at 40 ml/min., hydrogen at 20 ml/min. and helium at 80 ml/min. On the primer layer, cobalt was obliquely deposited in an oxygen atmosphere to form a cobalt oxide layer of 0.15 μm in thickness. Thereafter, a Si—C—O protective layer having a thickness of 200 Å was formed by using a FR power source of 13.56 MHz and 1 kW with supplying (CH$_3$O)$_3$Si—O—Si(OCH$_3$)$_3$ at 20 ml/min., oxygen at 40 ml/min., hydrogen at 20 ml/min. and helium at 80 ml/min.

The compositions of the Si—C—O, Si—N—O and Si—B—O protective layers and the Si—C—O primer layer were analyzed by the XPS. The results are shown in Table 6.

TABLE 6

| Example No. | Primer layer | Protective layer | Composition |
|---|---|---|---|
| Example 46 | — | Si-C-O | Si:C:O = 1:0.13:1.83 |
| Example 47 | — | Si-C-O | Si:C:O = 1:0.12:1.84 |
| Example 48 | — | Si-C-O | Si:C:O = 1:0.14:1.85 |
| Example 49 | — | Si-C-O | Si:C:O = 1:0.12:1.85 |
| Example 50 | — | Si-C-O | Si:C:O = 1:0.13:1.83 |
| Example 51 | — | Si-N-O | Si:N:O = 1:0.08:1.87 |
| Example 52 | — | Si-B-O | Si:B:O = 1:0.09:1.86 |
| Example 53 | Si-C-O | | Si:C:O = 1:0.12:1.85 |
| Example 53 | | Si-C-O | Si:C:O = 1:0.13:1.87 |
| Example 54 | Si-C-O | | Si:C:O = 1:0.14:1.85 |
| Example 54 | | Si-C-O | Si:C:O = 1:0.11:1.86 |
| Example 55 | Si-C-O | | Si:C:O = 1:0.13:1.84 |
| Example 55 | | Si-C-O | Si:C:O = 1:0.14:1.87 |

As seen from the results in Table 6, the compositions of all the protective layers and the primer layer were in the range of Si:M (C, B or N):O=1:(0.05–0.5):(1.60–2.0).

Comparative Example 9

On a polyethylene naphthalate film having a thickness of 4 μm, cobalt was obliquely deposited in an oxygen atmosphere to form a cobalt oxide layer of 0.15 μm in thickness, but no protective layer was formed on the cobalt oxide layer.

Each of the samples produced in Examples 49 and 54 and Comparative Example 9 was maintained in an atmosphere of 60° C. and 90% RH, and change of saturation magnetization was monitored. The results are shown in Table 7.

TABLE 7

| Example | | Change of saturation magnetization (%) after | | | |
|---|---|---|---|---|---|
| No. | Structure | 1 day | 7 days | 14 days | 21 days |
| C. Ex. 9 | Co-O/PEN | −2.5 | −9.5 | −16.5 | −22.3 |
| Ex. 49 | Si-C-O/ Co-O/PEN | −1.0 | −2.5 | −6.0 | −10.8 |
| Ex. 54 | Si-C-O/ Co-O/ Si-C-O/ PEN | −0.3 | −1.1 | −1.8 | −2.3 |

From the results in Table 7, it is understood that, in comparison with the sample of Comparative Example 9 having no protective layer, the decrease of saturation magnetization could be suppressed in the sample having the Si—C—O protective layer of Example 49, and among three samples, the decrease of saturation magnetization was lowest in the sample having both the primer layer and the protective layer of Example 54.

Example 56

Each of the samples produced in Examples 46–55 was dipped in a 0.2 wt. % solution of the compound prepared in Example 1 in n-hexane for 30 seconds, pulled up and dried. Then, the film was cut to a width of 8 mm, and its still durability was measured. The still durability was measured by winding the tape around a cylinder at a winding angle of 220 degrees under a tension of 12.5 gf/cm on the tape at a relative speed of 11.3 m/sec. in an atmosphere of normal temperature and normal humidity.

During the still durability measurement, a load on the cylinder was measured as described above.

Comparative Example 10

On a polyethylene naphthalate film having a thickness of 4 μm, cobalt was obliquely deposited in an oxygen atmosphere to form a cobalt oxide layer of 0.15 μm in thickness. The sample was dipped in a 0.2 wt. % solution of Fomblin Z-DOL in perfluorooctane for 30 seconds, pulled up and dried. Then, the film was cut to a width of 8 mm, and its still durability and a load on the cylinder were measured in the same manner as in Example 56.

Comparative Example 11

On a polyethylene naphthalate film having a thickness of 4 μm, cobalt was obliquely deposited in an oxygen atmosphere to form a cobalt oxide layer of 0.15 μm in thickness. On the cobalt oxide layer, a Si—C—O protective layer having a thickness of 200 Å was formed by using a FR power source of 13.56 MHz and 1 kW with supplying $(CH_3O)_3Si—O—Si(OCH_3)_3$ at 20 ml/min., oxygen at 40 ml/min., hydrogen at 20 ml/min. and helium at 80 ml/min. The sample was dipped in a 0.2 wt. % solution of Fomblin Z-DOL in perfluorooctane for 30 seconds, pulled up and dried. Then, the film was cut to a width of 8 mm, and its still durability and a load on the cylinder were measured in the same manner as in Example 56.

The results of the still test are shown in Table 8.

The still life is a time (min.) at which the reproducing output decreased to a half of the original output.

As seen from those results, the samples of the present inventions had the still durability of longer than 240 minutes, and the load on the cylinder in the present invention was about 25% smaller than that in Comparative Example 10 using the conventional perfluoropolyether liquid lubricant.

TABLE 8

| Example No. | Still life (min.) | Load on cylinder (mV) |
|---|---|---|
| Example 46 | >240 | 40 |
| Example 47 | >240 | 40 |
| Example 48 | >240 | 44 |
| Example 49 | >240 | 40 |
| Example 50 | >240 | 40 |
| Example 51 | >240 | 42 |
| Example 52 | >240 | 40 |
| Example 53 | >240 | 42 |
| Example 54 | >240 | 40 |
| Example 55 | >240 | 40 |
| Comp. Ex. 10 | 1 | 45 |
| Comp. Ex. 11 | 55 | 67 |

Example 57

On a polyethylene naphthalate film having a thickness of 4 μm, a Si—C—O primer layer having a thickness of 200 Å was formed by using a FR power source of 13.56 MHz and 1 kW with supplying $(CH_3O)_3Si—O—Si(OCH_3)_3$ at 20 ml/min., oxygen at 40 ml/min., hydrogen at 20 ml/min. and helium at 80 ml/min. On the primer layer, cobalt was obliquely deposited in an oxygen atmosphere to form a cobalt oxide layer of 0.15 μm in thickness. Thereafter, a Si—C—O protective layer having a thickness of 200 A was formed by using a FR power source of 13.56 MHz and 1 kW with supplying $(CH_3O)_3Si—O—Si(OCH_3)_3$ at 20 ml/min., oxygen at 40 ml/min., hydrogen at 20 ml/min. and helium at 80 ml/min.

Then, the film was dipped in a 0.2 wt. % solution of the compound prepared in Example 1 in n-hexane for 30 seconds, pulled up and dried.

An amount of the lubricant on the protective layer was measured by the XPS as follows:

The sample was set in a vacuum chamber. After evacuating the chamber, the sample was irradiated by UV light having a wavelength of 185 nm from a low pressure mercury lamp provided in the chamber for 10 seconds to 10 minutes. After UV light irradiation, the sample was cleaned in n-hexane with applying ultrasonic wave, and an amount of the lubricant remaining on the protective layer was measured by the XPS, and expressed by the 1s peak intensity of fluorine atoms. The results are shown in Table 9.

TABLE 9

| | F1s peak intensity | F1s (UV)/ F1s (Initial)[1] |
|---|---|---|
| Coating only | 25.0 | — |
| Coating + Cleaning | 2.6 | 0.11 |
| Coating + UV, 10 sec. + Cleaning | 3.8 | 0.15 |
| Coating + UV, 30 sec. + Cleaning | 4.8 | 0.20 |
| Coating + UV, 60 | 6.6 | 0.25 |

TABLE 9-continued

| | F1s peak intensity | F1s (UV)/ F1s (Initial)[1] |
|---|---|---|
| sec. + Cleaning | | |
| Coating + UV, 2 min. + Cleaning | 8.5 | 0.32 |
| Coating + UV, 5 min. + Cleaning | 12.0 | 0.47 |
| Coating + UV, 7 min. + Cleaning | 15.0 | 0.58 |
| Coating + UV, 10 min. + Cleaning | 22.0 | 0.88 |

Note:
[1]A ratio of the 1s peak intensity of F after the UV light irradiation and ultrasonic wave cleaning to that before the UV light irradiation and ultrasonic wave cleaning.

Example 58

The sample produced in Example 57 was cut to a width of 8 mm to form a magnetic tape, and its still durability was measured. The still durability was measured by winding the tape around a cylinder at a winding angle of 220 degrees under a tension of 12.5 gf/cm on the tape at a relative speed of 11.3 m/sec. in an atmosphere of normal temperature and normal humidity.

During the still durability measurement, a load on the cylinder was measured as described above.

The results are shown in Table 10.

From the results in Table 10, it is understood that the samples having the F1s (UV)/F1s (initial) ratio of 0.05 to 0.65 in Table 9 after UV light irradiation had the still durability of longer than 4 hours, and the load on the cylinder was decreased by the UV light irradiation.

When the UV light was irradiated for 10 minutes, the F1s (UV)/F1s (initial) ratio exceeded 0.65, so that the still durability was again shortened since the amount of the free molecules of the lubricant was insufficient.

TABLE 10

| Sample | Still life (min.) | Load on cylinder (mV) |
|---|---|---|
| Coating only | >240 | 42 |
| Coating + Cleaning | 20 | 65 |
| Coating + UV, 10 sec. + Cleaning | >240 | 40 |
| Coating + UV, 30 sec. + Cleaning | >240 | 42 |
| Coating + UV, 60 sec. + Cleaning | >240 | 38 |
| Coating + UV, 2 min. + Cleaning | >240 | 38 |
| Coating + UV, 5 min. + Cleaning | >240 | 36 |
| Coating + UV, 7 min. + Cleaning | >240 | 36 |
| Coating + UV, 10 min. + Cleaning | 150 | 36 |

Example 59

On a polyethylene naphthalate film having a thickness of 4 μm and different surface roughness, cobalt was obliquely deposited in an oxygen atmosphere to form a cobalt oxide layer of 0.15 μm in thickness. Thereafter, a Si—C—O protective layer having a thickness of 200 Å was formed by using a FR power source of 13.56 MHz and 1 kW with supplying $(CH_3O)_3Si—O—Si(OCH_3)_3$ at 20 ml/min., oxygen at 40 ml/min., hydrogen at 20 ml/min. and helium at 80 ml/min.

Then, the film was dipped in a 0.2 wt. % solution of the compound prepared in Example 1 in n-hexane for 30 seconds, pulled up and dried.

The sample was maintained in an atmosphere of 60° C. and 90% RH for 14 days, and change of saturation magnetization was monitored.

The film was cut to a width of 8 mm and the tape was wound around a cylinder at a winding angle of 220 degrees under a tension of 12.5 gf/cm on the tape, and sticking of the tape to the cylinder was observed at normal temperature and normal humidity.

The results are shown in Table 11.

TABLE 11

| Smoothness of PEN | | Change of saturation magnetization | Presence of sticking to |
|---|---|---|---|
| Ra (nm) | Rz (nm) | (%) | cylinder |
| 0.5 | 3.0 | −4.0 | No |
| 1.0 | 10.8 | −6.2 | No |
| 1.4 | 11.5 | −9.0 | No |
| 3.9 | 19.5 | −13.5 | No |

As seen from the above results of Table 11, when the substrate film having the high smoothness was used, the decrease of the saturation magnetization was small, and the corrosion resistance was improved. Even when the substrate film having the high smoothness, the tape was not stuck to the cylinder.

Comparative Example 12

On a polyethylene naphthalate film having a thickness of 4 μm and different surface roughness as used in Example 59, cobalt was obliquely deposited in an oxygen atmosphere to form a cobalt oxide layer of 0.15 μm in thickness. Thereafter, a Si—C—O protective layer having a thickness of 200 Å was formed by using a FR power source of 13.56 MHz and 1 kW with supplying $(CH_3O)_3Si—O—Si(OCH_3)_3$ at 20 ml/min., oxygen at 40 ml/min., hydrogen at 20 ml/min. and helium at 80 ml/min.

Then, the film was dipped in a 0.2 wt. % solution of the perfluoropolyether liquid lubricant Fomblin Z-DOL in perfluoro-octane for 30 seconds, pulled up and dried.

The film was cut to a width of 8 mm and the tape was wound around a cylinder at a winding angle of 220 degrees under a tension of 12.5 gf/cm on the tape, and sticking of the tape to the cylinder was observed at normal temperature and normal humidity.

In all cases, the tapes were stuck to the cylinder.

What is claimed is:

1. A magnetic recording medium comprising a non-magnetic substrate, a magnetic layer formed on at least one surface of said non-magnetic substrate, and a lubricant layer which is present on or in said magnetic layer and comprises an organic compound of the formula (1):

$$R_1\text{-}Z_1\text{-}R_3\text{-}Z_2\text{-}R_2 \qquad (1)$$

wherein $R_1$ and $R_2$ are the same and different and represent a linear, branched or cyclic saturated or unsaturated hydrocarbon group, a polyether group, a polyester group, a polyamide group or a polycarbonate group each of which has 4 to 34 carbon atoms; $Z_1$ and $Z_2$ are the same or different and represent an amide bond, an ether bond, a urethane bond, a urea bond or an amine salt bond formed by a reaction between an acid and an amine; and $R_3$ is a group of the formula:

$$-(CH_2)_x-(CF_2)_y-(CH_2)_z-$$

in which x and z are the same or different and an integer of 1 to 4, and y is an integer of 4 to 34.

2. A magnetic recording medium comprising a non-magnetic substrate, a magnetic layer formed on at least one surface of said non-magnetic substrate, a protective layer comprising a film of an oxide of the formula:

$$SiM_wO_v$$

wherein v is a number of larger than 1.6 and smaller than 2.0, w is larger than 0.05 and smaller than 0.5, and M is an at least one element selected from carbon, nitrogen or boron, and a lubricant which is formed on said protective layer and comprises an organic compound of the formula (1):

$$R_1\text{-}Z_1\text{-}R_3\text{-}Z_2\text{-}R_2 \qquad (1)$$

wherein $R_1$ and $R_2$ are the same and different and represent a linear, branched or cyclic saturated or unsaturated hydrocarbon group, a polyether group, a polyester group, a polyamide group or a polycarbonate group each of which has 4 to 34 carbon atoms; $Z_1$ and $Z_2$ are the same or different and represent an amide bond, an ether bond, a urethane bond, a urea bond or an amine salt bond formed by a reaction between an acid and an amine; and $R_3$ is a group of the formula:

$$-(CH_2)_x-(CF_2)_y-(CH_2)_z-$$

in which x and z are the same or different and an integer of 1 to 4, and y is an integer of 4 to 34.

3. The magnetic recording medium according to claim 2, wherein a thickness of said protective layer is from 50 to 300 Å.

4. The magnetic recording medium according to claim 2, which further comprises an intermediate layer having a thickness of 50 to 1000 Å and comprising a film of a an oxide of the formula:

$$SiM_wO_v$$

wherein v is a number of larger than 1.6 and smaller than 2.0, w is larger than 0.05 and smaller than 0.5, and M is an at least one element selected from carbon, nitrogen or boron, between said non-magnetic substrate and said magnetic layer.

5. The magnetic recording medium according to claim 2, which further comprises a back coating layer having a thickness of 50 to 1000 Å and comprising a film of a an oxide of the formula:

$$SiM_wO_v$$

wherein v is a number of larger than 1.6 and smaller than 2.0, w is larger than 0.05 and smaller than 0.5, and M is an at least one element selected from carbon, nitrogen or boron, on a surface of said non-magnetic substrate opposite to said magnetic layer.

6. The magnetic recording medium according to claim 2, wherein said non-magnetic substrate consists of a synthetic resin film having a thickness of 6.5 μm or less selected from the group consisting of a polyethylene terephthalate film, a polyethylene naphthalate film and an aramide film.

7. A magnetic recording medium comprising a non-magnetic substrate, a magnetic layer formed on said non-magnetic substrate, and optionally a protective layer formed on said magnetic layer, wherein a lubricant layer which comprises an organic compound of the formula (1):

$$R_1\text{-}Z_1\text{-}R_3\text{-}Z_2\text{-}R_2 \qquad (1)$$

wherein $R_1$ and $R_2$ are the same and different and represent a linear, branched or cyclic saturated or unsaturated hydrocarbon group, a polyether group, a polyester group, a polyamide group or a polycarbonate group each of which has 4 to 34 carbon atoms; $Z_1$ and $Z_2$ are the same or different and represent an amide bond, an ether bond, a urethane bond, a urea bond or an amine salt bond formed by a reaction between an acid and an amine; and $R_3$ is a group of the formula:

$$-(CH_2)_x-(CF_2)_y-(CH_2)_z-$$

in which x and z are the same or different and an integer of 1 to 4, and y is an integer of 4 to 34 is formed on said lubricant layer or said optional protective layer, said lubricant layer is irradiated by UV light, and when said lubricant layer is subjected to ultrasonic washing in a non-fluorine solvent for 10 seconds and analyzed by X-ray photoelectron spectroscopy using, a ratio of an intensity of fluorine peak after washing to that before washing is from 0.05:1 to 0.65:1.

8. The magnetic recording medium according to claim 7, wherein said non-fluorine solvent is at least one solvent selected from the group consisting of n-hexane, n-heptane, n-octane, n-decane, n-dodecane, benzene, toluene, xylene, cyclohexane, acetone, methyl ethyl ketone, methyl isobutyl ketone, methanol, ethanol, isopropanol, diethyl ether, cyclohexanone and tetrahydrofuran.

9. The magnetic recording medium according to claim 8, wherein said non-fluorine solvent is n-hexane.

* * * * *